United States Patent [19]

Münz et al.

[11] 3,933,463

[45] Jan. 20, 1976

[54] HERBICIDALLY ACTIVE IMIDAZOLIDIN-2-ON-1-CARBOXYLIC ACID AMIDES

[75] Inventors: Ferdinand Münz, Schildgen; Helmuth Hack, Cologne-Buchheim; Ludwig Eue, Cologne-Stammheim, all of Germany

[73] Assignee: Bayer Aktiengesellschaft, Leverkusen, Germany

[22] Filed: July 28, 1969

[21] Appl. No.: 845,540

[30] Foreign Application Priority Data
Aug. 13, 1968 Germany.............................. 1795117

[52] U.S. Cl. ................................................. 71/92
[51] Int. Cl.² ........................................... A01N 9/22
[58] Field of Search ........................................ 71/92

[56] References Cited
UNITED STATES PATENTS
3,234,000  2/1966  Bartels.................................. 71/92

OTHER PUBLICATIONS
Tilley et al., J. Org. Chem. 29, (1964), pp. 3347–3350, (cited by applicant).

Primary Examiner—Glennon H. Hollrah
Attorney, Agent, or Firm—Burgess, Dinklage & Sprung

[57] ABSTRACT

Compositions and methods of using certain imidazolidin-2-on-1-carboxylic acid amides, i.e. imidazolidin-2-on-1-carboxylic acid alkyl and alkenyl amides, some of which are known, which possess strong herbicidal properties, and which may be produced by conventional methods.

13 Claims, No Drawings

HERBICIDALLY ACTIVE IMIDAZOLIDIN-2-ON-1-CARBOXYLIC ACID AMIDES

The present invention relates to and has for its objects the provision for particular new active compositions in the form of mixtures with solid and liquid dispersible carrier vehicles of certain imidazolidin-2-on-1-carboxylic acid amides, i.e. imidazolidin-2-on-1-carboxylic acid alkyl and alkenyl amides, some of which are known, and which possess valuable selective herbicidal properties, and methods for using such compounds in a new way, especially for combating and controlling plants, e.g. weeds, with other and further objects becoming apparent from a study of the within specification and accompanying examples.

It is known that ureas, such as N-(3,4-dichlorophenyl)-N'-methyl-N'-n-butyl urea (A) [compare U.S. Pat. No. 2,655,444], or biurets, such as 1-phenyl-3-phenyl-5,5-dimethyl biuret (B) [compare German Patent No. 1,032,595], can be used as herbicides.

In this regard, the known members of the class of imidazolidin-2-on-1-carboxylic acid amides to which the present invention relates are not yet known to have any pesticidal properties, and in fact most of the instant compounds of this class of imidazolidin-2-on-1-carboxylic acid amides are still unknown per se.

It has now been found, in accordance with the present invention, that certain imidazolidin-2-on-1-carboxylic acid amides, some of which are known, of the formula

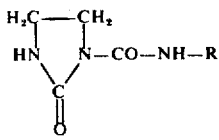
(Ia)

in which
R is alkyl of 1-4 carbon atoms or alkenyl of 3-4 carbon atoms, exhibit strong, especially selective, herbicidal properties.

It has been furthermore found, in accordance with the present invention, that the compounds of formula (Ia) above may be produced by the process which comprises reacting an imidazolidin-2-on-1-carbonyl chloride of the formula:

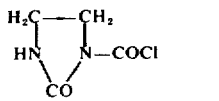
(II)

in the presence of an acid-binding agent and water, with a primary amine of the formula:
R—NH$_2$ (III)
in which R is the same as defined above.

It is very surprising that the active compounds of formula (Ia) above usable according to the present invention exhibit, with equal herbicidal potency, a substantially better selective herbicidal activity when compared with chemically similar compounds, such as ureas and biurets, for example N-(3,4-dichlorophenyl)-N'-methyl-N'-n-butyl urea (A) and 1-phenyl-3-phenyl-5,5-dimethyl biuret (B). Therefore, the present invention represents a valuable contribution to the art.

The active compounds are clearly characterized by formula (Ia) above.

Advantageously, in accordance with the present invention, in the various formulae herein:

R represents
straight and branched chain lower alkyl hydrocarbon of 1-4 carbon atoms such as methyl, ethyl, n- and iso-propyl, n-, iso-, sec.- and tert.-butyl, and the like, especially C$_{2-4}$ or C$_{3-4}$ alkyl, more especially branched C$_{3-4}$ alkyl, and most especially isopropyl, isobutyl and tert.-butyl; or straight and branched chain lower alkenyl hydrocarbon of 3-4 carbon atoms such as α-, β- and γ- allyl (i.e. prop2-enyl, 1-methyl-vinyl and prop-1-enyl or crotonyl), but-1,2 and 3-enyl, 1-methyl-prop- 1 and 2-enyl, 1- and 2-methylprop-2-enyl, 1ethyl-vinyl, and the like, especially C$_3$ alkenyl, more especially allyl, and most especially α-allyl or prop-2-enyl.

Preferably, R is C$_{3-4}$ branched chain alkyl or C$_3$ alkenyl, especially α-allyl.

These compounds of formula (Ia) above usable according to the present invention are known in part (see J.Org. Chem. 29 (1968), 3347-3350).

Examples of starting amines which can be used for the preparation of the instant active compounds include methyl amine, ethyl amine, n-propyl amine, iso-propyl amine, allyl amine (i.e. prop-2-enyl amine), n-butyl amine, iso-butyl amine, tert.-butyl amine, and the like.

The preparation of the starting imidazolidin-2-on-1-carbonyl chloride can be effected according to various methods. It is obtained in a particularly simple manner from ethylene-urea and phosgene (J. Org. Chem. 29 (1964), 2401-2404).

The production reaction according to the present invention is, as mentioned above, effected in the presence of water, i.e. as diluent. Surprisingly, water is more suitable than inert organic diluents, such as benzene and toluene, although carbonyl chlorides, in particular N-carbonyl chlorides, are in general very sensitive to water. In this connection, for example, the comparable allophanic acid chloride, H$_2$N—CO—N-H—COCl, decomposes very vigorously in water (compare German Pat. No. 238,961).

The acid-binding agent to be used may for example be any of the customary acid-binding substances. Preferred examples include alkali metal hydroxides and alkaline earth metal hydroxides; alkaline earth metal carbonates and alkali metal carbonates; tertiary amines, such as pyridine; and the like, or an excess of the starting amine used for the reaction. Sodium hydroxide solution has proved particularly suitable, in this regard.

The reaction temperature can be varied within a fairly wide range. In general, the work is carried out at substantially between about 0°-80°C, preferably between about 20°-50°C.

The production process may be carried out in the following typical way:

1 mol of imidazolidin-2-on-1-carbonyl chloride is stirred with an amount of water to give a readily stirrable suspension. 1 to 1.2 mols of amine and 1 mol of sodium hydroxide solution are then run in simultaneously in such a manner that the amine is always present in small excess. After the running in has been completed, stirring is continued until the mixture is cold. The precipitated reaction product is filtered off with suction and washed with water. It is usually of good purity and, in general, does not need to be specially purified.

Advantageously, the active compounds according to the present invention exhibit a strong herbicidal potency and can therefore be used as weed killers. By weeds are meant in the broadest sense all plants which grow in places where they are not desired. Whether the active compounds according to the present invention act as total or selective herbicidal agents depends primarily on the amount of active compound applied, as the artisan will appreciate.

The active compounds according to the present invention can be used for example in the case of the following plants: dicotyledons, such as mustard (Sinapis), cress (Lepidium), cleaver (Galium), common chickweed (Stellaria), mayweed (Matricaria), deadnettle (Lamium), small-flower Galinsoga (Galinsoga), fathen (Chenopodium), stinging nettle (Urtica), groundsel (Senecio), cotton (Gossypium), beets (Beta), carrots (Daucus), beans (Phaseolus), potatoes (Solanum), coffee (Coffea); monocotyledons, such as blackgrass (Alopecurus), timothy (Phelum), bluegrass (Poa), fescue (Festuca), goosegrass (Eleusine), foxtail (Setaria), ryegrass (Lolium), cheat (Bromus), barnyard grass (Echinochloa), maize (Zea), rice (Oryzae), oats (Avena), barley (Hordeum), wheat (Triticum), millet (Panicum) sugar cane (Saccharum); and the like.

The instant active compounds are preferably used as selective herbicides. Such active compounds exhibit a particularly good selectivity when used in beets, cotton and in cereals, particularly wheat.

The active compounds according to the instant invention can be utilized, if desired, in the form of the usual formulations or compositions with conventional inert (i.e. plant compatible or herbicidally inert) pesticidal diluents or extenders, i.e. diluents or extenders of the type usable in conventional pesticidal formulations or compositions, e.g. conventional pesticidal dispersible carrier vehicles, such as solutions, emulsions, suspensions, emulsifiable concentrates, spray powders, pastes, soluble powders, dusting agents, granules, etc. These are prepared in known manner, for instance by extending the active compounds with conventional pesticidal dispersible liquid diluent carriers and/or dispersible solid carriers optionally with the use of carrier vehicle assistants, e.g. conventional pesticidal surfaceactive agents, including emulsifying agents and/or dispersing agents, whereby, for example, in the case where water is used as diluent, organic solvents may be added as auxiliary solvents. The following may be chiefly considered for use as conventional carrier vehicles for this purpose: inert dispersible liquid diluent carriers including inert organic solvents, such as aromatic hydrocarbons (e.g. benzene, toluene, xylene, etc.), halogenated, especially chlorinated, aromatic hydrocarbons (e.g. chloro-benzenes), paraffins (e.g. petroleum fractions), chlorinated aliphatic hydrocarbons (e.g. methylene chloride, etc.), alcohols (e.g. methanol, ethanol, propanol, butanol, etc.), ethers, ether-alcohols (e.g. glycol monomethyl ether, etc.), amines (e.g. ethanol-amine, etc.), amides (e.g. dimethyl formamide, etc.), sulfoxides (e.g. dimethyl sulfoxide, etc.), ketones (e.g. acetone, etc.), and/or water; as well as inert dispersible finely divided solid carriers, such as ground natural minerals (e.g. kaolins, alumina, silica, chalk, i.e. calcium carbonate, talc, kieselguhr, etc.), and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfonates, aryl sulfonates, etc., and especially alkyl aryl-polyglycol ethers, magnesium stearate, sodium oleate, etc.); and/or dispersing agents, such as lignin, sulfite waste liquors, methyl cellulose, etc.

As will be appreciated by the artisan, the active compounds according to the instant invention may be employed alone or in the form of mixtures with one another and/or with such solid and/or liquid dispersible carrier vehicles and/or with other known compatible active agents, especially plant protection agents, such as other herbicides, or fungicides, insecticides, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1 and 95% by weight, and preferably 0.5 and 90% by weight, of the mixture, whereas carrier composition mixtures suitable for direct application or field application generally contemplate those in which the active compound is present in an amount substantially between about 0.005–0.5%, preferably 0.01–0.1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.005-95%, and preferably 0.01-95%, by weight of the mixture.

In particular, the amount of active compound applied per unit area varies according to the purpose intended, i.e. the effect desired, and the mode of application. In general, substantially between about 0.5–25 kg of active compound per hectare are applied, preferably between about 1.0–20 kg of active compound per hectare, irrespective of the presence or absence of the carrier vehicle.

The active compounds can also be used in accordance with the well-known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 1 quart/acre, preferably 2–16 fluid ounces/acre, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

While the active compounds can be used effectively according to the pre-emergence method, they are also particularly effective when used according to the post-emergence method.

In particular, in the usual aqueous preparations, and in the case of application after emergence, the concentration of the active compound is, in general, substantially between about 0.005–0.5%, and preferably between about 0.01–0.1%, by weight of the mixture with the carrier vehicle, as aforesaid.

Furthermore, the present invention contemplates methods of selectively killing, combatting or controlling undesired plants, e.g. weeds and the like, which comprise applying to at least one of (a) such weeds and (b) their habitat, i.e. the locus to be protected, a herbicidally effective or toxic amount of the particular compound of the invention alone or together with a carrier vehicle as noted above. The instant formulations or compositions are applied in the usual manner, for example by spraying, atomizing, vaporizing, scattering, dusting, watering, sprinkling, squirting, and the like, whether for pre-emergence application to the soil or post-emergence application to the weeds.

It will be realized, of course, that in connection with the pre-emergence use of the instant compounds as well as the post-emergence use thereof, the concentration of the particular active compound utilized, alone or in admixture with the carrier vehicle, will depend upon the intended application, as the artisan will appreciate, and may be varied within a fairly wide range depending upon the weather conditions, the purpose for which the active compound is used, e.g. for total or only selective herbicidal effect, and the plants which are to be controlled or protected. Therefore, in special cases, it is possible to go above or below the aforementioned concentration ranges and amounts per unit area.

The following Examples illustrate, without limitation, the herbicidal activity of the particular active compounds of the present invention.

EXAMPLE 1

Pre-emergence test

Solvent: 5 parts by weight acetone
Emulsifier: 1 part by weight alkylaryl polyglycol ether To produce a suitable preparation of the particular active compound, 1 part by weight of such active compound is mixed with the stated amount of solvent, the stated amount of emulsifier is added thereto, and the resulting concentrate is then diluted with water to the desired final concentration.

Seeds of the test plants are sown in normal soil and, after 24 hours, watered with the preparation of the given active compound. It is expedient to keep constant the amount of water per unit area. The concentration of the active compound in the given preparation is of no importance, only the amount of active compound applied per unit area being decisive. After three weeks, the degree of damage to the test plants is determined and characterized by the values 0–5, which have the following meaning:

0 no effect
1 slight damage or delay in growth
2 marked damage or inhibition of growth
3 heavy damage and only deficient development or only 50% emerged
4 plants partially destroyed after germination or only 25% emerged
5 plants completely dead or not emerged.

The particular active compounds tested, the amounts applied and the results obtained can be seen from the following Table 1.

Table 1

| Active compound | Pre-emergence test Active comp. applied in kg/hectare | Beet | Cotton | Mustard | Galinsoga | Lamium | Chenopodium |
|---|---|---|---|---|---|---|---|
| (A) Cl-C6H3(Cl)-NH-C(O)-N(CH3)(CH2-CH2-CH2-CH3) (known) | 5<br>2.5 | 5<br>5 | 3<br>1 | 5<br>4.5 | 5<br>5 | 3<br>2 | 5<br>4 |
| (B) C6H5-NH-C(O)-N(C6H5)-C(O)-N(CH3)2 (known) | 5<br>2.5 | 5<br>3.5 | 2<br>1 | 5<br>4.5 | 5<br>5 | 4<br>3 | 5<br>4 |
| (1₁) HN(CH2CH2)N-C(O)-NH-C(CH3)3 (with C=O ring) | 5<br>2.5 | 3<br>1 | 1<br>0 | 5<br>5 | 5<br>5 | 5<br>4.5 | 5<br>4 |

Table 1-continued

| Active compound | Pre-emergence test | | | | | | | |
|---|---|---|---|---|---|---|---|---|
| | | Active comp. applied in kg/hectare | Beet | Cotton | Mustard | Galinsoga | Lamium | Chenopodium |
| (2₁) HN–N–C(=O)–NH–CH₂–CH=CH₂ (with C=O bridge) | | 5<br>2.5 | 1<br>0 | 0<br>0 | 5<br>4.5 | 5<br>5 | 4<br>3 | 5<br>4 |
| (3₁) HN–N–C(=O)–NH–CH(CH₃)CH₃ (with C=O bridge) | | 5<br>2.5 | 2<br>0 | 4<br>2 | 5<br>5 | 5<br>5 | 5<br>4.5 | 5<br>5 |
| (4₁) HN–N–C(=O)–NH–CH₂–CH(CH₃)CH₃ (with C=O bridge) | | 5<br>2.5 | 0<br>0 | 0<br>0 | 5<br>5 | 5<br>5 | 5<br>4.5 | 5<br>5 |

EXAMPLE 2

Post-emergence test

Solvent: 5 parts by weight acetone
Emulsifier: 1 part by weight alkylaryl polyglycol ether To produce a suitable preparation of the particular active compound, 1 part by weight of such active compound is mixed with the stated amount of solvent, the stated amount of emulsifier is added thereto and the resulting concentrate is then diluted with water to the desired final concentration.

Test plants which have a height of about 5–5 cm. are sprayed with the preparation of the given active compound until just dew moist. After three weeks, the degree of damage to the plants is determined and characterized by the values 0–5, which have the following meaning:

0 no effect
1 a few slightly burnt spots
2 marked damage to leaves
3 some leaves and parts of stalks partially dead
4 plant partially destroyed
5 plant completely dead.

The particular active compounds tested, their concentrations and the results obtained can be seen from the following Table 2.

Table 2

| Active compound | Post-emergence test | | | | | |
|---|---|---|---|---|---|---|
| | Concentration of active compound in % | Beets | Wheat | Mustard | Galinsoga | Matricaria |
| (A) Cl₂-C₆H₃–NH–C(=O)–N(CH₃)(CH₂CH₂CH₂CH₃) (known) | 0.1<br>0.05 | 4<br>2 | 1<br>0 | 3<br>2 | 4<br>3 | 1<br>0 |
| (B) C₆H₅–NH–C(=O)–N(C₆H₅)–C(=O)–N(CH₃)₂ (known) | 0.1<br>0.05 | 3<br>1 | 2<br>1 | 4<br>2 | 5<br>4 | 4<br>3 |

Table 2-continued

| Active compound | Post-emergence test Concentration of active compound in % | Beets | Wheat | Mustard | Galinsoga | Matricaria |
|---|---|---|---|---|---|---|
| (1₂) HN—N—C—NH—C(CH₃)₃ (imidazolidinone carbonyl) | 0.1<br>0.05 | 2<br>0 | 1<br>0 | 5<br>4 | 5<br>4 | 4<br>3 |
| (2₂) HN—N—C—NH—CH₂—CH=CH₂ | 0.1<br>0.05 | 0<br>0 | 0<br>0 | 4<br>2 | 4<br>3 | 3.5<br>2 |
| (3₂) HN—N—C—NH—CH(CH₃)₂ | 0.1<br>0.05 | 2<br>0 | 1<br>0 | 5<br>4 | 5<br>4.5 | 5<br>4 |
| (4₂) HN—N—C—NH—CH₂—CH(CH₃)₂ | 0.1<br>0.05 | 0<br>0 | 1<br>0 | 5<br>4.5 | 5<br>4.5 | 5<br>4 |

The following further examples are set forth to illustrate, without limitation, the manner of producing the active compounds according to the present invention:

EXAMPLE 3

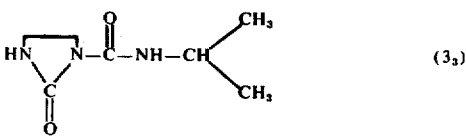

(3₃)

148.5 g imidazolidin-2-on-1-carbonyl chloride are stirred with 100 ml of water. To this mixtue there are added dropwise from one dropping funnel 65 g isopropyl amine and, from a second dropping funnel, 100 ml sodium hydroxide solution with a content of 40 g NaOH in such a manner that the pH value does not rise above 10. The temperature is kept to 35° to 40°C by cooling. When the entire amount of the amine has been added dropwise, the pH value is raised to 12 by the remainder of the sodium hydroxide solution. Stirring until cold is effected; the product is filtered off with suction and washed with a little water. The yield of imidazolidin-2-on-1-carboxylic acid isopropyl amide is 116 g (68% of the theory). The melting point is 125° to 127°C; after recrystallization from ethyl acetate, the melting point is 126° to 127°C.

EXAMPLE 4

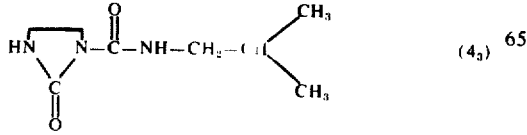

(4₃)

When, in accordance with the procedure of Example 3, the isopropyl amine is replaced by 77 g isobutyl amine, 159 g (86% of the theory) of imidazolidin-2-on-1-carboxylic acid isobutyl amide which melts at 95° to 96°C are obtained.

EXAMPLE 5

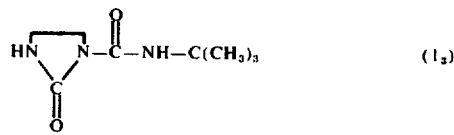

(1₃)

When 80 g tert.-butyl amine are used in the process described in Example 3, 137 g (74% of the theory) of imidazolidin-2-on-1-carboxylic acid tert.-butyl amide having a melting point of 153° to 154°C can be isolated.

EXAMPLE 6

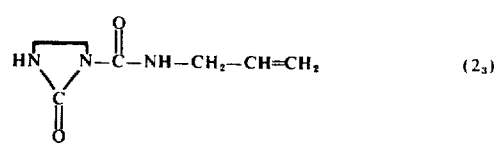

(2₃)

68 g allyl amine (i.e. prop-2-enyl amine) are reacted in the manner described in Example 3, and 130 g (77% of the theory) of imidazolidin-2-on-1-carboxylic acid allyl amide which melts at 75° to 76°C are obtained.

It will be realized by the artisan that all of the foregoing compounds contemplated by the present invention possess the desired strong and selective herbicidal properties, and especially the capability of controlling and destroying selectively weeds, as well as a comparatively low toxicity toward warm-blooded creatures, enabling such compounds to be used with correspondingly favorable compatibility with respect to warm-blooded creatures for more effective control and/or elimination of weeds by application of such compounds to such weeds and/or their habitat. As contemplated herein, the term "weeds" is meant to include not only weeds in the narrow sense, but also weeds, and especially plants, in the broad sense, whereby to cover all plants and vegetation considered undesirable for the particular purposes in question.

It will be appreciated that the instant specification and examples are set forth by way of illustration and not limitation, and that various modifications and changes may be made without departing from the spirit and scope of the present invention.

What is claimed is:

1. Herbicidal composition which consists essentially of a mixture of a dispersible carrier vehicle selected from the group consisting of (1) a finely divided dispersible carrier solid containing a surface-active agent selected from the group consisting of non-ionic emulsifying agents, anionic emulsifying agents, dispersing agents, and mixtures of such agents, and (2) a dispersible carrier liquid selected from the group consisting of inert organic solvents, water, and mixtures thereof, and containing a surface-active agent selected from the group consisting of non-ionic emulsifying agents, anionic emulsifying agents, dispersing agents, and mixtures of such agents, and a herbicidally effective amount, constituting substantially between about 0.005–95% by weight of the mixture, and sufficient to combat weeds, of an imidazolidin-2-on-1-carboxylic acid amide of the formula

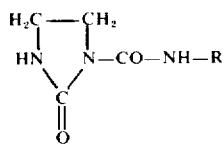

in which R is selected from the group consisting of alkyl of 1–4 carbon atoms and alkenyl of 3–4 carbon atoms.

2. Method of killing weeds, which comprises applying to at least one of (a) such weeds and (b) their habitat, a herbicidally effective amount of an imidazolidin-2-on-1-carboxylic acid amide of the formula

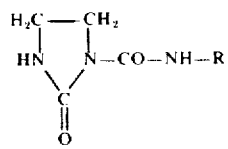

in which R is selected from the group consisting of alkyl of 1–4 carbon atoms and alkenyl of 3–4 carbon atoms.

3. Method according to claim 2 wherein R is selected from the group consisting of $C_{3-4}$ branched chain alkyl and $C_3$ alkenyl.

4. Method according to claim 2 wherein such compound is used in the form of a mixture with a dispersible carrier vehicle, said compound being present in a herbicidally effective amount and constituting substantially between about 0.005–95% by weight of the mixture.

5. Method according to claim 2 wherein such compound is imidazolidin-2-on-1-carboxylic acid tert.-butyl amide of the formula

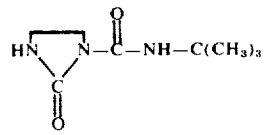

6. Method according to claim 2 wherein such compound is imidazolidin-2-on-1-carboxylic acid allyl amide of the formula

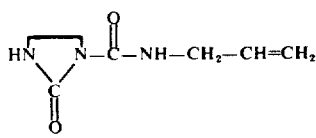

7. Method according to claim 2 wherein such compound is imidazolidin-2-on-1-carboxylic acid isopropyl amide of the formula

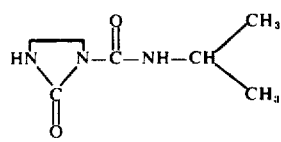

8. Method according to claim 2 wherein such compound is imidazolidin-2-on-1-carboxylic acid isobutyl amide of the formula

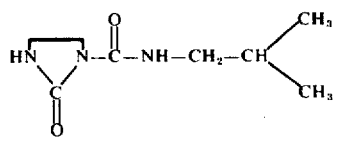

9. Composition as claimed in claim 1 wherein R in the formula is selected from the group consisting of branched chain alkyl having from 3 to 4 carbon atoms and of alkenyl having 3 carbon atoms.

10. Composition as claimed in claim 1 wherein said amide is imidazolidin-2-on-1-carboxylic acid tert.-butyl amide.

11. Composition as claimed in claim 1 wherein said amide is imidazolidin-2-on-1-carboxylic acid allyl amide.

12. Composition as claimed in claim 1 wherein said amide is imidazolidin-2-on-1-carboxylic acid isopropyl amide.

13. Composition as claimed in claim 1 wherein said amide is imidazolidin-2-on-1-carboxylic acid isobutyl amide.

* * * * *